US00RE40305E

(19) United States
(12) Reissued Patent
Richter

(10) Patent Number: US RE40,305 E
(45) Date of Reissued Patent: May 6, 2008

(54) APPARATUS AND METHOD FOR SELECTIVELY POSITIONING A DEVICE AND MANIPULATING IT

(75) Inventor: Jacob Richter, Ramat Hasharon (IL)

(73) Assignee: Zuli Holdings Ltd., Ramat Hasharon (IL)

(21) Appl. No.: 10/193,201

(22) Filed: Sep. 19, 2002

Related U.S. Patent Documents

Reissue of:
(64) Patent No.: 6,238,401
Issued: May 29, 2001
Appl. No.: 09/127,222
Filed: Jul. 31, 1998

(51) Int. Cl.
*A61M 31/00* (2006.01)

(52) U.S. Cl. ..... 606/108; 604/95.01; 128/898

(58) Field of Classification Search ..... 606/1, 606/108, 159, 190–200; 604/264, 164.01, 604/523–536; 600/434, 585, 126; 623/1, 623/11

See application file for complete search history.

(56) References Cited

U.S. PATENT DOCUMENTS

| | | | | |
|---|---|---|---|---|
| 3,760,203 A | * | 9/1973 | Guntersdorfer et al. | 310/317 |
| 4,389,208 A | | 6/1983 | LeVeen et al. | |
| 4,747,407 A | | 5/1988 | Liu et al. | |
| 4,854,325 A | | 8/1989 | Stevens | |
| 4,886,061 A | | 12/1989 | Fischell et al. | |
| 4,946,466 A | | 8/1990 | Pinchuk et al. | |
| 5,243,997 A | * | 9/1993 | Uflacker et al. | 600/585 |
| 5,287,858 A | | 2/1994 | Hammerslag et al. | |
| 5,304,115 A | | 4/1994 | Pflueger et al. | |
| 5,318,541 A | | 6/1994 | Viera et al. | |
| 5,328,471 A | | 7/1994 | Slepian | |
| 5,380,273 A | | 1/1995 | Dubrul et al. | |
| 5,380,274 A | | 1/1995 | Nita | |

(Continued)

FOREIGN PATENT DOCUMENTS

| | | | | |
|---|---|---|---|---|
| DE | 4329162 A1 | | 3/1995 | |
| EP | 0541258 A1 | | 5/1993 | |
| GB | 2 328 877 | * | 3/1999 | |
| GB | 2328877 A | | 3/1999 | |
| JP | 2129193 | | 10/1990 | |
| JP | 2-129193 | | 10/1990 | |
| JP | 04-176770 | | 6/1992 | |
| JP | 05084296 | * | 4/1993 | 604/187 |
| JP | 5-58338 | | 8/1993 | |
| JP | 6269185 | | 9/1994 | |
| JP | 7156843 | | 6/1995 | |
| JP | 8207755 | | 8/1996 | |
| JP | 8216876 | | 8/1996 | |
| JP | 9037571 | | 2/1997 | |
| JP | 10-113396 | | 5/1998 | |
| JP | 10113396 | | 5/1998 | |
| JP | 10-165510 | | 6/1998 | |
| WO | 95/32539 | | 11/1995 | |
| WO | 98/30266 | * | 7/1998 | 604/159 |

*Primary Examiner*—Glenn K. Dawson
(74) *Attorney, Agent, or Firm*—Cadwalader Wickersham & Taft LLP

(57) ABSTRACT

Apparatus for pulling and positioning an apparatus, e.g., a stent, in the target area of a lumen. In one embodiment, a cylindrically shaped motor has a longitudinal bore, a friction area within the longitudinal bore, and a guide wire disposed within the longitudinal bore. The guide wire and friction area of the motor are sized and adapted to contact each other and impart friction between the friction area and the guide wire to permit the motor to pull a catheter to the target arcs by crawling against the guide wire. In another embodiment, a cylindrical motor having a friction area on its outer surface is disposed within a guide tube.

65 Claims, 6 Drawing Sheets

U.S. PATENT DOCUMENTS 5,389,100 A 2/1995 Bacich et al.
5,453,653 A 9/1995 Zumeris
5,498,236 A 3/1996 Dubrul et al.
5,499,632 A 3/1996 Hill, III et al.
5,501,228 A 3/1996 Lafontaine et al.
5,549,119 A 8/1996 Solar
5,571,114 A 11/1996 Devamabpuoma
5,628,719 A * 5/1997 Hastings et al. ..... 600/16
5,632,755 A 5/1997 Nordgren et al.
5,643,297 A 7/1997 Nordgren et al.
5,643,298 A 7/1997 Nordgren et al.
5,662,587 A * 9/1997 Grundfest et al. ..... 600/114
5,662,609 A 9/1997 Slepian
5,707,376 A 1/1998 Kavteladze et al.
5,713,848 A 2/1998 Dubrul et al.
5,746,758 A 5/1998 Nordgren et al.
5,776,153 A 7/1998 Rees
5,908,395 A 6/1999 Stalker et al.
6,001,112 A 12/1999 Taylor
6,183,432 B1 2/2001 Milo
6,184,609 B1 * 2/2001 Johansson et al. ..... 310/328
6,228,046 B1 5/2001 Brisken
6,238,401 B1 5/2001 Richter
6,258,052 B1 7/2001 Milo
6,287,271 B1 9/2001 Dubrul et al.
6,290,675 B1 * 9/2001 Vujanic et al. ..... 604/159
6,302,875 B1 10/2001 Makower et al.
6,348,040 B1 2/2002 Stalker et al.

* cited by examiner

APPARATUS AND METHOD FOR SELECTIVELY POSITIONING A DEVICE AND MANIPULATING IT

Matter enclosed in heavy brackets [ ] appears in the original patent but forms no part of this reissue specification; matter printed in italics indicates the additions made by reissue.

FIELD OF THE INVENTION

This invention relates generally to an apparatus and method of selectively positioning the apparatus, e.g., within a lumen. More particularly, this invention relates to a device and method for pulling a catheter along a wire; a device and method for moving a wire relative to a catheter, a device and method for pulling a catheter relative to a guiding catheter or any larger bore pipeline through which it is inserted; and a device and method for pushing or pulling a device on top of a guide wire or inside a guiding catheter.

BACKGROUND OF THE INVENTION

In many different applications of invasive and minimally invasive medicine there is a need to introduce catheters and other devices into the body, usually through open lumens or closed lumens, utilizing percutaneous entry. Conventional procedures for the introduction of the devices and their controlled motion in the body usually utilize a force, either a manual force or a motorized force, applied from the outside of the patient to "push" the device to the target area. One shortcoming of introducing the device via a "push" operation, even when done on top of a guiding wire, is that this procedure often does not provide optimal [tractability] *trackability* into [a] tortuous anatomy, e.g., the coronary arteries. In contrast, a "pull" operation in which a pulling device precedes the apparatus and "pulls" it into place increases the [tractability] *trackability* of the device and reduces the likelihood that the device will get caught in a curve of the lumen or cause trauma to the lumen.

Another problem is the need to push wires through occluded lumen sections that have a great resistance to such penetration. The fact that the wire is pushed from the outside may waste all the pushing energy in accessive loops with very little or none of the pushing energy actually reaching the tip of the wire.

OBJECTS AND SUMMARY OF THE INVENTION

It is an object of this invention to provide a device and method for pulling a catheter along a wire.

It is another object of this invention to provide a device and method for pushing a wire relative to a catheter.

In yet another object of this invention to provide a device and method for pulling a catheter relative to a guiding catheter or any larger bore pipeline through which it is inserted.

It is a further object of this invention to provide a device and method for pushing or pulling a device on top of a guidewire or inside a guiding catheter.

It is still a further object of this invention to provide an apparatus and method for selectively positioning a device, e.g., a stent, an Intra Vascular Sound (IVUS) transducer, an atherectomy device (both rotational and directional), pressure sensors, balloons, and pushing wires to open occlusions, by pulling rather than pushing these devices into place.

It is an object of this invention to provide an apparatus for disposing a device in the target area of a lumen, comprising: a cylindrically shaped motor attached to the device, the motor having a longitudinal bore, the motor provided with a motor friction area disposed within the longitudinal bore; a guide wire disposed within the longitudinal bore, the guide wire and the longitudinal bore sized and adapted to impart friction between the friction area of the motor and the guide wire in an amount sufficient to permit the motor to change position relative to the guide wire by crawling against the guide wire when the motor is energized.

It is another object of this invention to provide an apparatus for disposing a device in the target area of a lumen, comprising: a cylindrically shaped motor attached to the device, the motor having an outer surface, the motor provided with a friction area on the outer surface; a cylindrical guide tube having an outer surface and an inner surface defining a longitudinal bore, the outer surface of the motor and the inner surface of the guide tube sized and adapted to impart friction between the friction area of the motor and the inner surface of the cylindrical guide tube in an amount sufficient to permit the cylindrical motor to change position relative to the guide tube by crawling against the inner surface of the guide tube when the motor is energized.

It is still another object of this invention to provide an apparatus for disposing a stent in the target area of a lumen, comprising: a catheter having a proximal end, a distal end, a longitudinal bore therethrough, and an expandable balloon disposed at the distal end; a cylindrically shaped motor disposed at the distal end of the catheter distal to the balloon, the motor having a longitudinal bore communicating with the longitudinal bore of the catheter, the motor provided with a motor friction area disposed within the longitudinal bore; a guide wire disposed with the longitudinal bore of the catheter and the longitudinal bore of the motor, the guide wire and the longitudinal bore of the motor sized and adapted to impart friction between the friction area of the motor and the guide wire in an amount sufficient to permit the motor to change position relative to the guide wire by crawling against the guide wire when the motor is energized.

It is another object of this invention to provide a method of disposing a stent in the target area of a lumen, comprising the steps of:

a) constructing an apparatus comprising: a catheter having a proximal end, a distal end, a longitudinal bore therethrough, and an expandable balloon disposed at the distal end; a cylindrically shaped motor disposed at the distal end of the catheter distal to the balloon, the motor having a longitudinal bore communicating with the longitudinal bore of the catheter, the motor provided with a motor friction area disposed within the longitudinal bore, a guide wire disposed within the longitudinal bore of the catheter and the longitudinal bore of the motor, the guide wire and the longitudinal bore of the motor sized and adapted to impart friction between the friction area of the motor and the guide wire in an amount sufficient to permit the motor to change position relative to the guide wire by crawling against the guide wire when the motor is energized;

b) advancing the guide wire to the target area;

c) securing the guide wire;

d) energizing the motor so that it advances along the guide wire to the target area to dispose the stent in the target area of lumen;

e) inflating the balloon to secure the stent in the target area of the lumen;

f) deflating the balloon; and g) withdrawing the guide wire, motor, and catheter from the lumen.

It is yet another object of this invention to provide a method of disposing a stent in an obstructed target area of a lumen, comprising the steps of:

a) constructing an apparatus comprising: a catheter having a proximal end, a distal end, a longitudinal bore therethrough, and an expandable balloon disposed at the distal end; a cylindrically shaped motor disposed at the distal end of the catheter distal to the balloon, the motor having a longitudinal bore communicating with the longitudinal bore of the catheter, the motor provided with a motor friction area disposed within the longitudinal bore, a guide wire disposed with the longitudinal bore of the catheter and the longitudinal bore of the motor, the guide wire and the longitudinal bore of the motor sized and adapted to impart friction between the friction area of the motor and the guide wire in an amount sufficient to permit the motor to change position relative to the guide wire by crawling against the guide wire when the motor is energized;

b) advancing the guide wire to the target area;

c) securing the guide wire;

d) energizing the motor so that the motor advances along the guide wire to the obstructed target area;

e) securing the catheter;

f) energizing the motor so that the guide wire advances through the longitudinal bore of the motor and into the obstructed target area of the lumen;

g) securing the guide wire;

h) energizing the motor so that the motor advances along the guide wire and disposes the stent in the target area of the lumen;

i) inflating the balloon to secure the stent in the target area of the lumen;

j) deflating the balloon; and k) withdrawing the guide wire, motor, and catheter from the lumen.

*More generally, embodiments of the present invention employ a piezoelectric micromotor to move a device to a target area in a lumen. In one embodiment, the motor is attached to a catheter and frictionally engages a guide wire. Energizing the motor brings about relative motion between the wire and catheter. This allows moving the wire to a target area in a lumen with the catheter fixed and/or moving the catheter to the target area while holding the guide wire fixed. The catheter may have a balloon to be expanded in the lumen at the target area. Similarly, the catheter may deliver a stent to the target area where it can be expanded. When there is an obstruction that prevents reaching the target area, the guide wire and motor may be used to clear the obstruction to permit the guide wire and catheter to be moved to the target area.*

DETAILED DESCRIPTION OF THE INVENTION

Miniature Oscillating Ceramic Motors (OCM) are well known in the art and are disclosed in U.S. Pat. No. 5,453,653 to Zumeris the specification of which is incorporated herein by reference. These motors can be made very small and in any shape and they operate by contacting a surface in an amount sufficient to generate sufficient friction to permit the motor to "crawl" along the contacted surface and change its position relative to the contracted surface when the motor is energized. These motors can be adequately insulated to act in aqueous environments. Their small size and low energy level requirements make them especially suitable for use inside living organisms.

Figure 1:
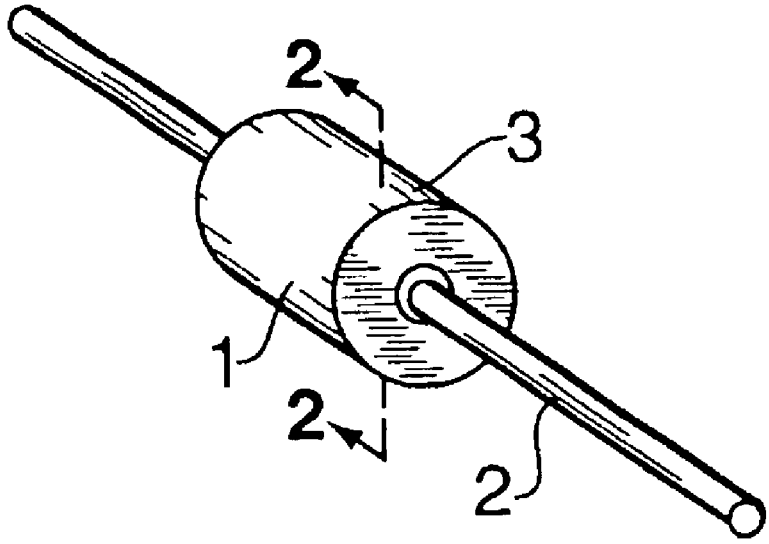
FIG. 1 shows an embodiment of the invention in which a cylindrically shaped motor and a guide wire are utilized to dispose a device in the target area of a lumen.
Figure 2:
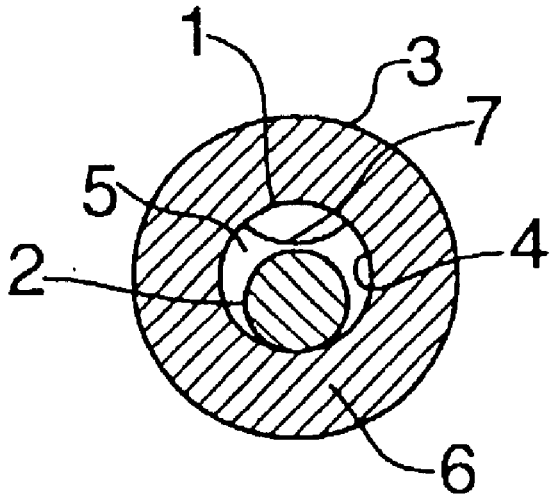
FIG. 2 is a cross-sectional end view of the embodiment of the invention shown in FIG. 1.

FIG. 1 is a lateral perspective of one embodiment of the invention and shows a cylindrical motor 1, *of the type described above in Zumeris,* having a longitudinal bore therethrough. A guide wire 2 is disposed within the longitudinal bore 5. FIG. 2 is a cross-sectional end view taken on line A-A of FIG. 1 and shows the cylindrical motor 1 having an outer surface 3 and an inner surface 4 defining a longitudinal bore 5. The inner surface 4 defining the longitudinal bore 5 is provided with a friction area 6 adapted to engage the guide wire 2. The longitudinal bore 5 and the guide wire 2 are sized and adapted so that when the motor 1 is energized the motor 1 will crawl along the guide wire 2, thus, changing its position relative to the guide wire 2. The direction of movement is controlled selectively by energizing wires (not shown) connected to the motor 1. In one embodiment, shown in FIG. 2, a biasing means, e.g., a leaf spring 7 is utilized to bias the guide wire 2 against the friction area 6 of the motor 1.

Figure 3:
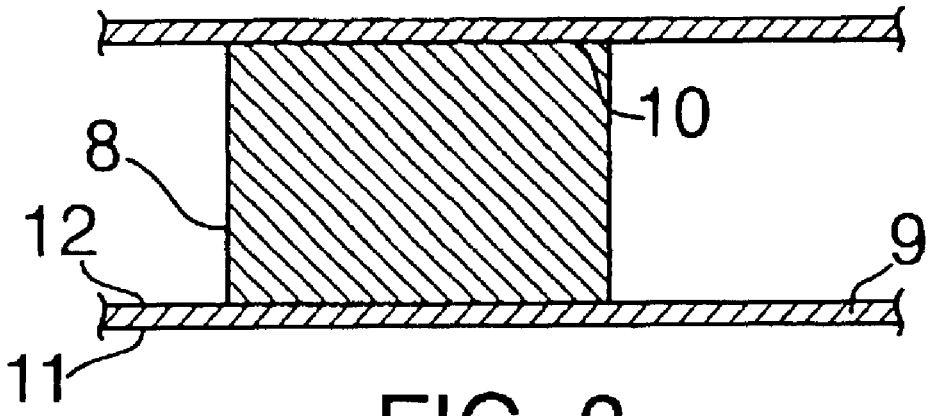
FIG. 3 shows an embodiment of the invention in which a cylindrical motor and a cylindrical guide tube are used to dispose a device in the target area of a lumen.
Figure 4:
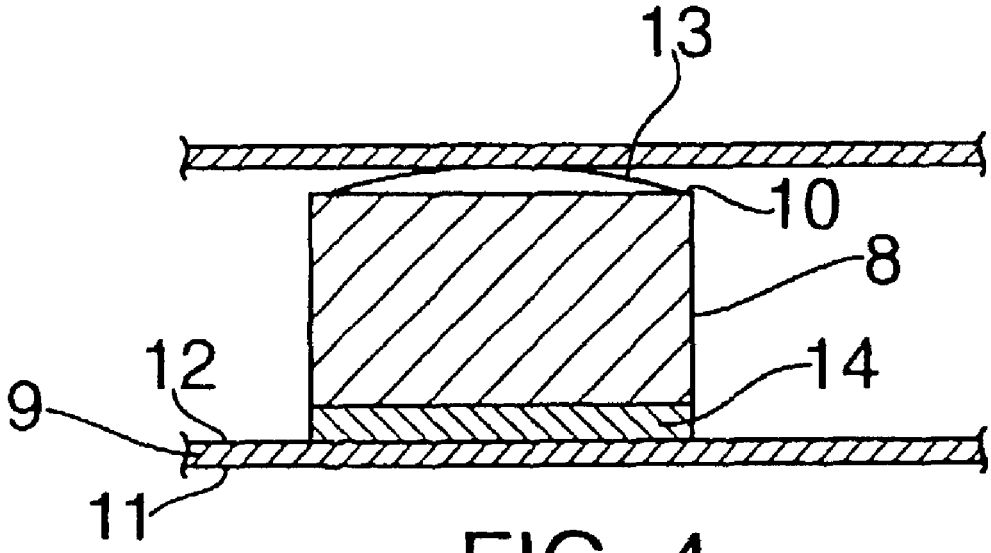
FIG. 4 shows a cross-sectional side view of another embodiment of the invention shown in FIG. 3.

FIG. 3 is a cross-sectional side view of another embodiment of the invention and shows a cylindrical motor 8 having an external surface 10 mounted within a guide tube 9 having and outer surface 11 and an inner surface 12. The external surface 10 of the motor 8 and the internal surface 12 of the guide tube 9 are sized and adapted so that the friction area 14 of the motor 8 contacts the inner surface 12 of the guide tube 9 and crawls along the inner surface 12 so as to dispose a device, e.g., an Intra Vascular Ultra Sound (IVUS) transducer, atherectomy device, or physiological sensor, (not shown) in the target area of a lumen. In an especially preferred embodiment, shown in FIG. 4, a leaf spring 13 is utilized to bias the friction surface 14 of the motor 8 against the internal surface 12 of the guide tube 9.

Figure 7:
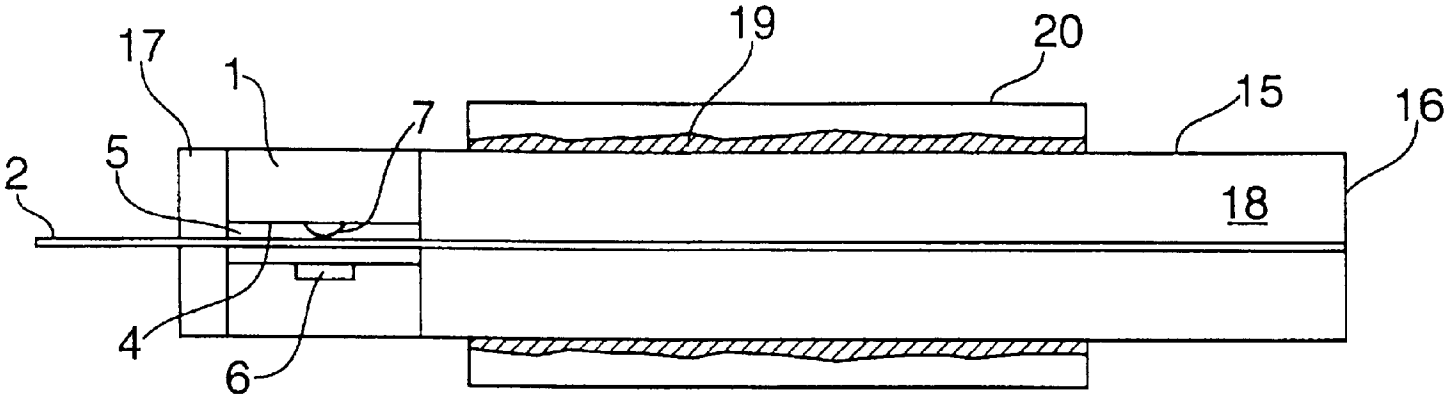
FIG. 7 shows an embodiment of the invention used to dispose a balloon expandable stent in the lumen of a blood vessel.

In another embodiment of this invention, shown in FIG. 7, a balloon catheter with a micro-motor disposed at the distal end is used to dispose an expandable stent in the target area of a lumen. FIG. 7 shows a catheter 15 having a proximal end 16, a distal end 17, and a longitudinal bore 18 therethrough. An expandable balloon 19 is disposed at the distal end 17. A cylindrically shaped motor 1 is disposed at the distal end 17 of the catheter 15 distal to the balloon 19. The motor 1 has a longitudinal bore 5 communicating with the longitudinal bore 18 of the catheter 15 and is provided with a motor friction area 6 disposed within the longitudinal bore 5 of the motor 1. The guide wire 2 is disposed within the longitudinal bore 18 of the catheter 15 and the longitudinal bore 5 of the motor 1. The guide wire 2 and the longitudinal bore 5 of the motor 1 are sized and adapted to impart friction between the friction area 6 of the motor 1 and the guide wire 2 in an amount sufficient to permit the motor 1 to change position relative to the guide wire 2 by crawling against the guide wire 2 when the motor 1 is energized.

Figure 6:
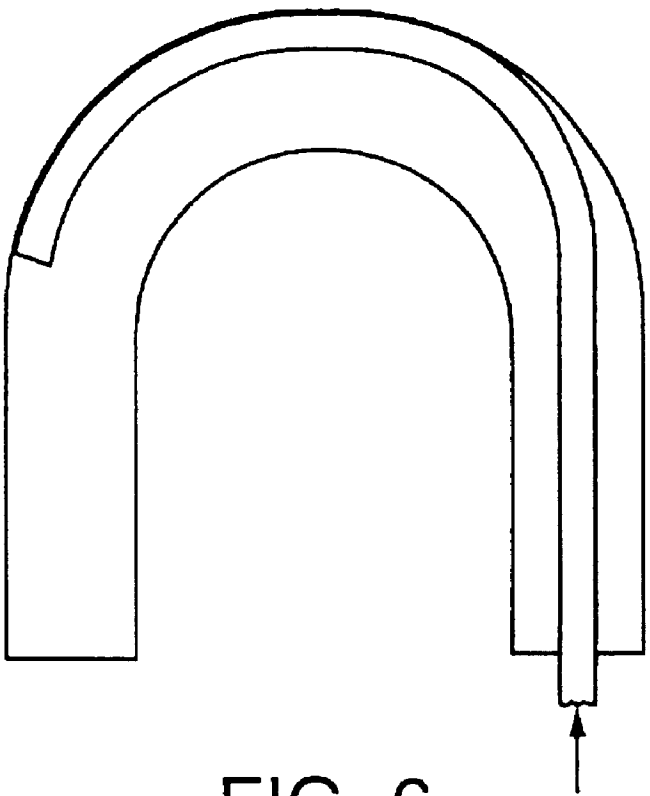
FIG. 6 shows the [tractability] *trackability* of a catheter that is pulled through a curve in a lumen in a conventional manner.
Figure 5:
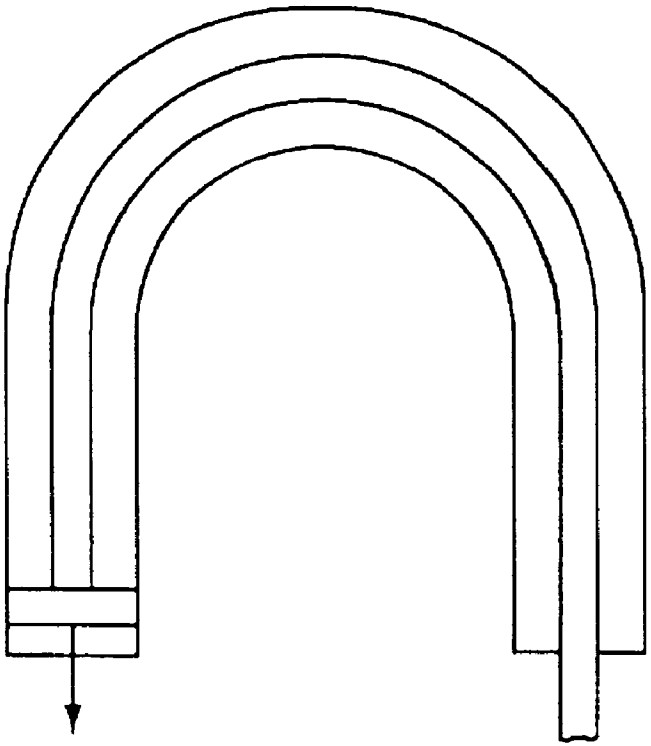
FIG. 5 shows the [tractability] *trackability* of a catheter that is pulled through a curve in a lumen in accordance with the present invention.

In operation, an expandable stent 20 is secured to the balloon portion 19 of the catheter 15 and the guide wire 2 is placed into the bore 18 of the catheter 15. The guide wire 2 is then introduced into the lumen to be treated and is advanced by pushing it until it is near the target area. The guide wire 2 is then secured. The micro-motor 1 is then energized so that it crawls along the guide wire 2 which pulls the catheter 15 into the proximity of the target area to be treated. Because the catheter 15 is "pulled" into position as shown in FIG. 5, there is improved [tractability] *trackability* and less kinking of the catheter 15, and, thus, reduced risk of trauma to the internal surface of the lumen than when the catheter is "pushed" into place using conventional procedures as shown in FIG. 6. The balloon 19 is then expanded to secure the stent 20 in the target area of the lumen. The balloon 19 is then deflated and the guide wire 2 and the catheter 15 are pulled out of the lumen using conventional methods.

Figure 8A:
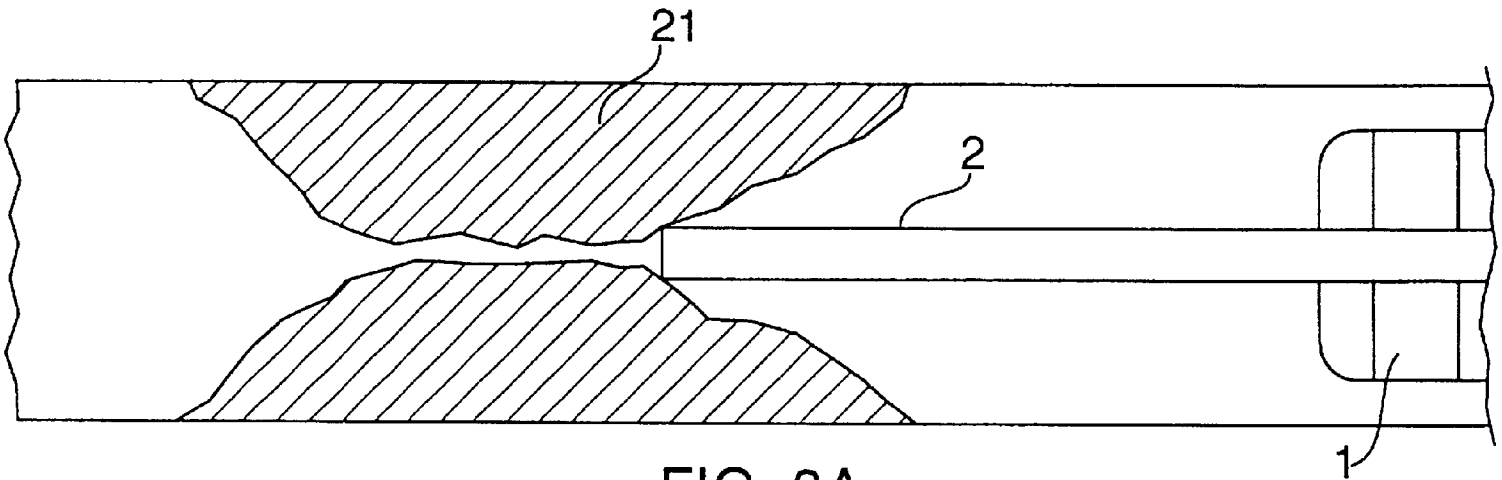
FIGS. 8A to 8D shows an embodiment of the invention used to clear an obstructed lumen.
Figure 8B:
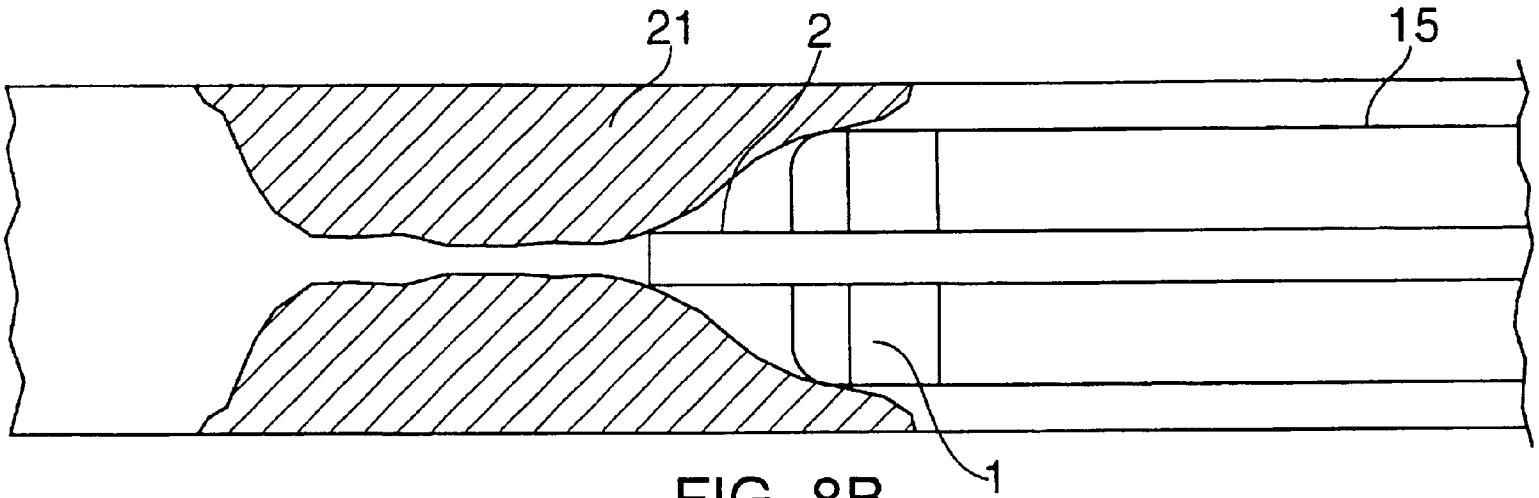
Figure 8C:
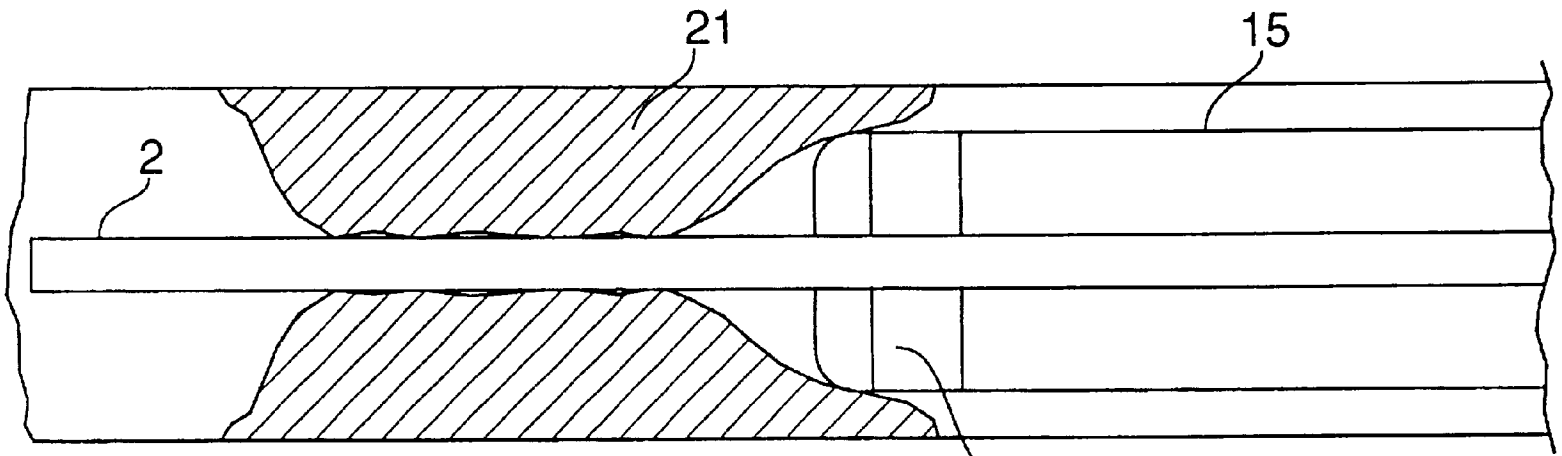

In another embodiment of this invention shown in FIGS. 8A to 8D, the motor is used to push the guide wire into, and if specific applications dictate through, a constricted area which clears the vessel of the obstruction to permit the catheter to advance beyond the obstruction to the target area. In operation, the catheter 15 is mounted on a guide wire 2 as previously discussed. The guide wire 2 is advanced to the obstruction 21 as shown in FIG. 8A. The guide wire 2 is secured and the motor is energized causing the catheter to advance towards the obstruction 21. The catheter 15 is advanced until it too is in proximity to the obstruction 21 as shown in FIG. 8B. The catheter 15 is then secured and the motor 1 is activated which causes the guide wire 2 to advance into the obstructed area 21 as shown in FIG. 8C.

In some applications, one or more passes may be utilized to clear the obstruction. *As has been recognized by those skilled in the art, vibrating the guide wire facilitates the wire passing through an obstruction. As explained in U.S. Pat. No. 5,453,653 to Zumeris, excitation of the micro-motor of the present invention with an AC voltage is possible. If excited with AC, a vibration in the range of 20-100 KHz., depending on the resonant frequency of the material used for the piezoelectric ceramic will result. As further explained, in a pulsed method of operation two electrodes are excited by a positive DC voltage and two electrodes are excited by a negative DC voltage. Under this excitation the left side of piezoelectric ceramic becomes longer than the right side and ceramic moves to the right. When the voltage is removed, the ceramic will move back to its original position. However, if a non-symmetrical voltage pulse is applied to the electrodes, then, during the return to zero, the inertia of body will cause the body not to return the ceramic to the starting position. Thus, when operating in the DC pulsed mode, a vibrating or pulsating motion will occur at a rate dependent on the pulse time, e.g., 10-50 ms. Stated another way, in each case, an oscillatory motion takes place.*

Figure 8D:
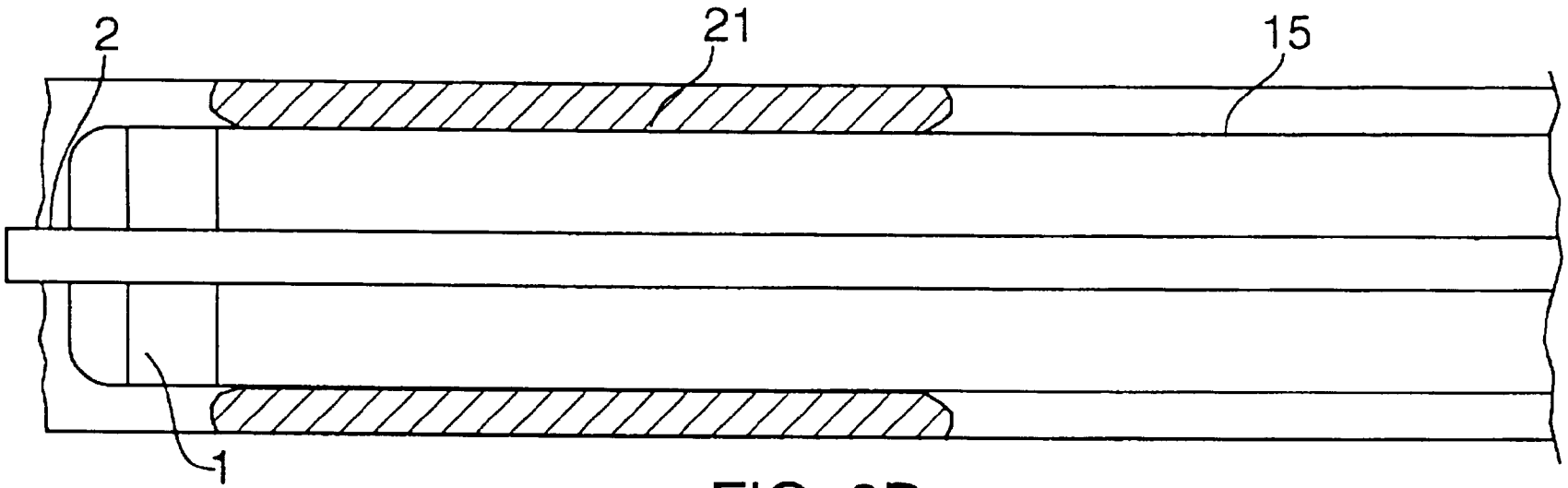

The guide wire 2 is then secured, the motor 1 is energized, and the catheter 15 is advanced through the vessel past the area from which the guide wire 2 has cleared the obstruction 21 from the target area as shown in FIG. 8D. This method may be used to simply clear an obstruction in a lumen as discussed above or may be used in conjunction with other embodiments of the invention, e.g., to facilitate the placement of an expandable stent in the target area of a lumen by first clearing the target area of any obstructions.

Figure 9:
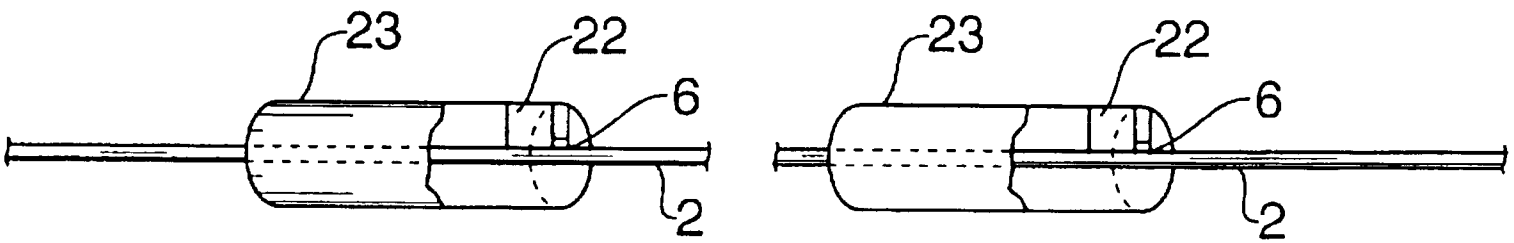
FIG. 9 shows an alternative embodiment of the invention.

FIG. 9 shows an alternative embodiment of the invention and shows a slab-shaped motor 22 incorporated in a catheter 23. In the embodiment shown in FIG. 9, the motor 22 is shaped like a slab instead of being cylindrical. The slab-shaped motor 22 is disposed on the inner wall of the catheter 23 and is provided with a friction area 6 sized and adapted to frictionally engage a guide-wire 2. The slab-shaped motor 22 is sized and adapted to permit the catheter 23 to be moved relative to the guide-wire 2 as previously discussed and as shown in FIG. 9.

While the invention has been described with respect to a limited number of embodiments, it will be appreciated that many variations, modifications, and other applications of the invention may be made.

What is claimed is:

1. An apparatus, comprising: a cylindrically shaped motor, said motor having a longitudinal bore, said motor provided with a motor friction area disposed within said longitudinal bore; a guide wire disposed within said longitudinal bore, said guide wire and said longitudinal bore sized and adapted to impart friction between said friction area of said motor and said guide wire in an amount sufficient to permit said motor to change position relative to said guide wire by crawling against said guide wire when said motor is energized; and, further comprising a biasing means to bias said guide wire against said friction area.

2. The apparatus of claim 1, wherein said biasing means is a leaf spring.

3. An apparatus, comprising: a cylindrically shaped motor, said motor having an outer surface, said motor provided with a friction area on said outer surface; a cylindrical guide tube having an outer surface and an inner surface defining a longitudinal bore, said outer surface of said motor and said inner surface of said guide tube sized and adapted to impart friction between said friction area of said motor and said inner surface of said cylindrical guide tube in an amount sufficient to permit said cylindrical motor to change position relative to said guide tube by crawling against said inner surface of said guide tube when said motor is energized.

4. The apparatus of claim 3, further comprising a biasing means to bias said inner surface of said guide tube against said friction area.

5. The apparatus of claim 4, wherein said biasing means is a leaf spring.

6. A method of disposing a device in the target area of a lumen, comprising the steps of:

a) constructing an apparatus comprising: a cylindrically shaped motor attached to said device, said motor having a longitudinal bore, said motor provided with a motor friction area disposed within said longitudinal bore, a guide wire disposed within said longitudinal bore, said guide wire and said longitudinal bore of said motor sized and adapted to impart friction between said friction area of said motor and said guide wire in an amount sufficient to permit said motor to change position relative to said guide wire by crawling against said guide wire when said motor is energized;

b) advancing said guide wire to said target area;

c) securing said guide wire;

d) energizing said motor so that said motor advances along said guide wire to said target area to dispose said device in said target area of said lumen; and e) withdrawing said guide wire, motor, and catheter from said lumen.

7. A method of disposing a device in the target area of a lumen, comprising the steps of:

a) constructing an apparatus comprising: a cylindrically shaped motor having an outer surface, said motor provided with a friction area on said outer surface, a cylindrical guide tube having an outer surface and an inner surface defining a longitudinal bore, said outer surface of said motor and said inner surface of said guide tube sized and adapted to impart friction between said friction area and said inner surface of said cylindrical guide tube in an amount sufficient to permit said cylindrical motor to change position relative to said guide tube by crawling against said inner surface of said guide tube when said motor is energized;

b) advancing said guide tube to said target area;

c) securing said guide tube;

d) inserting said motor attached to said device in said bore of said guide tube;

e) energizing said motor so that said motor advances along said inner surface of said guide tube to said target area to dispose said device in said target area of said lumen; and f) withdrawing said guide tube, motor, and catheter from said lumen.

8. An apparatus for disposing a stent in the target area of a lumen, comprising: a catheter having a proximal end, a distal end, a longitudinal bore therethrough, and an expandable balloon disposed at said distal end; a cylindrically shaped motor disposed at said distal end of said catheter distal to said balloon, said motor having a longitudinal bore communicating with a said longitudinal bore of said catheter, said motor provided with motor friction area disposed within said longitudinal bore of said motor; a guide wire disposed within said longitudinal bore of said catheter and said longitudinal bore of said motor, said guide wire and said longitudinal bore of said motor sized and adapted to impart friction between said friction area of said motor and said guide wire in an amount sufficient to permit said motor to change position relative to said guide wire by crawling against said guide wire when said motor is energized.

9. The apparatus of claim 8, further comprising a biasing means to bias said guide wire against said friction area.

10. The apparatus of claim 9, wherein said biasing means is a leaf spring.

11. A method of disposing a stent in the target area of a lumen, comprising the steps of:

a) constructing an apparatus comprising: a catheter having a proximal end, a distal end, a longitudinal bore therethrough, and an expandable balloon disposed at said distal end; a cylindrically shaped motor disposed at said distal end of said catheter distal to said balloon, said motor having a longitudinal bore communicating with said longitudinal bore of said catheter, said motor provided with a motor friction area disposed within said longitudinal bore of said motor, a guide wire disposed within said longitudinal bore of said catheter and said longitudinal bore of said motor, said guide wire and said longitudinal bore of said motor sized and adapted to impart friction between said friction area of said motor and said guide wire in an amount sufficient to permit said motor to change position relative to said guide wire by crawling against said guide wire when said motor is energized;

b) advancing said guide wire to said target area;

c) securing said guide wire;

d) energizing said motor so that it advances along said guide wire to said target area to dispose said stent in said target area of said lumen;

e) inflating said balloon to secure said stent in said target area of said lumen;

f) deflating the balloon; and g) withdrawing said guide wire, motor, and catheter from said lumen.

12. A method of disposing a stent in an obstructed target area of a lumen, comprising the steps of:

a) constructing an apparatus comprising: a catheter having a proximal end, a distal end, a longitudinal bore therethrough, and an expandable balloon disposed at said distal end; a cylindrically shaped motor disposed at said distal end of said catheter distal to said balloon, said motor having a longitudinal bore communicating with said longitudinal bore of said catheter, said motor provided with a motor friction area disposed within said longitudinal bore, a guide wire disposed within said longitudinal bore of said catheter and said longitudinal bore of said motor, said guide wire and said longitudinal bore of said motor sized and adapted to impart friction between said friction area of said motor and said guide wire in an amount sufficient to permit said motor to change position relative to said guide wire by crawling against said guide wire when said motor is energized;

b) advancing said guide wire to said target area;

c) securing said guide wire;

d) energizing said motor so that said motor advances along said guide wire to said obstructed target area;

e) securing said catheter;

f) energizing said motor so that said guide wire advances through said longitudinal bore of said motor and into said obstructed target area of said lumen;

g) securing said guide wire;

h) energizing said motor so that said motor advances along said guide wire and disposes said stent in said target area of said lumen;

i) inflating said balloon to secure said stent in said target area of said lumen;

j) deflating the balloon; and k) withdrawing said guide wire, motor, and catheter from said lumen.

*13. A method comprising:*

*a) inserting a guide wire into of a catheter to which a micro-motor is attached, the guide wire passing through the catheter and operatively coupled to the micro-motor, into a lumen;*

*b) advancing the guide wire to a target area;*

*c) securing the guide wire;*

*d) energizing the micro-motor so that the micro-motor advances along the guide wire to target area, carrying with it the attached catheter.*

*14. The method according to claim 13 and further including:*

*e) withdrawing the guide wire, micro-motor, and catheter from the lumen.*

*15. The method according to claim 14 wherein a balloon is disposed on the distal end of the catheter and further including, prior to withdrawing the guide wire, micro-motor, and catheter from the lumen:*

*a) inflating the balloon in the target area of the lumen; and*

*b) deflating the balloon.*

*16. The method according to claim 15 wherein a stent is disposed over the balloon and the inflating of the balloon in the target area of the lumen expands the stent to dispose it in the target area.*

*17. The method according to claim 14 wherein a stent is provided at the distal end of the catheter and further comprising expanding the stent in the target area of the lumen to dispose it in the target area prior to withdrawing the guide wire, micro-motor, and catheter from the lumen.*

*18. A method comprising:*

*a) inserting a guide wire into a catheter to which a micro-motor is attached, the guide wire operatively coupled to the micro-motor, into a lumen in which there is an obstruction;*

*b) advancing the guide wire to a proximal end of the obstruction;*

*c) securing the guide wire;*

*d) energizing the micro-motor so that the micro-motor advances distally along the guide wire, carrying with it the attached catheter, toward the proximal end of the obstruction;*

*e) securing the catheter;*

*f) energizing the micro-motor so that the guide wire advances distally.*

*19. The method according to claim 18 wherein said energizing the micro-motor so that the guide wire advances distally comprises energizing in an oscillatory manner.*

*20. The method according to claim 19 wherein said micro-motor is a piezoelectric motor and said energizing comprises energizing with an AC voltage, thereby introducing a vibration to said guide wire.*

*21. The method according to claim 20 wherein said AC voltage has a frequency in the range of 20-100 kHz.*

*22. The method according to claim 19 wherein said micro-motor is a piezoelectric motor and said energizing comprises energizing with a pulsed DC voltage thereby imparting a pulsating motion to said guide wire.*

*23. The method according to claim 18 and further comprising disposing said guide wire within a bore in said motor.*

*24. The method according to claim 23 wherein said micro-motor is cylindrical with a bore, and said guide wire is passed through said bore of said micro-motor.*

*25. The method according to claim 18 wherein said step of energizing the motor so that the guide wire advances distally comprises repeatedly, until said guidewire and catheter pass substantially through said obstruction:*

*a) securing the catheter;*

*b) energizing the micro-motor so that the guide wire advances distally;*

*c) securing the guide wire;*

*d) energizing the micro-motor so that the micro-motor advances along the guide wire, carrying with it the attached catheter.*

*26. The method according to claim 25 wherein said steps b) and d) comprise energizing in an oscillatory manner.*

*27. The method according to claim 26 wherein said micro-motor is a piezoelectric motor and said energizing comprises energizing with an AC voltage, thereby introducing a vibration to said guide wire.*

*28. The method according to claim 27 wherein said AC voltage has a frequency in the range of 20-100 kHz.*

*29. The method according to claim 26 wherein said micro-motor is a piezoelectric motor and said energizing comprises energizing with an pulsed DC voltage thereby imparting a pulsating motion to said guide wire.*

*30. The method according to claim 25 and further including withdrawing the guide wire, motor, and catheter from the lumen.*

*31. The method according to claim 18 wherein said step of energizing the motor so that the guide wire advances distally comprises alternatively:*

*a) energizing the motor so that the guide wire advances distally;*

*b) energizing the motor so that the guide wire advances proximally; and*

*c) repeating steps a) and b) a plurality of times.*

*32. The method according to claim 31 comprising repeating steps a) and b) until the guide wire has substantially cleared the obstruction.*

*33. The method according to claim 32 and further including withdrawing the guide wire, motor, and catheter from the lumen.*

*34. The method according to claim 33 wherein said obstruction is at or proximal to a target area of the lumen and wherein a balloon is disposed on the distal end of the catheter and further including, prior to withdrawing the guide wire, motor, and catheter from the lumen:*

*a) inflating the balloon in the target area of the lumen; and*

*b) deflating the balloon.*

*35. The method according to claim 34 wherein a stent is disposed over the balloon and the inflating of the balloon in the target area of the lumen expands the stent to dispose it in the target area.*

*36. The method according to claim 33 wherein a stent is provided at the distal end of the catheter and further comprising expanding the stent in the target area of the lumen to dispose it in the target area prior to withdrawing the guide wire, motor, and catheter from the lumen.*

*37. The method according to claim 31 wherein said steps a) and b) comprise energizing in an oscillatory manner.*

*38. The method according to claim 37 wherein said micro-motor is a piezoelectric motor and said energizing comprises energizing with an AC voltage, thereby introducing a vibration to said guide wire.*

*39. The method according to claim 38 wherein said AC voltage has a frequency in the range of 20-100 kHz.*

*40. The method according to claim 37 wherein said micro-motor is a piezoelectric motor and said energizing comprises energizing with an pulsed DC voltage thereby imparting a pulsating motion to said guide wire.*

*41. The method according to claim 18 wherein said step f) comprises energizing the motor so that the guide wire advances through the obstruction.*

*42. The method according to claim 41 wherein said energizing the micro-motor so that the guide wire advances through the obstruction comprises energizing in an oscillatory manner.*

*43. The method according to claim 42 wherein said micro-motor is a piezoelectric motor and said energizing*

*comprises energizing with an AC voltage, thereby introducing a vibration to said guide wire.*

*44. The method according to claim 43 wherein said AC voltage has a frequency in the range of 20-100 kHz.*

*45. The method according to claim 42 wherein said micro-motor is a piezoelectric motor and said energizing comprises energizing with an pulsed DC voltage thereby imparting a pulsating motion to said guide wire.*

*46. The method according to claim 45 and further comprising disposing said guide wire within a bore in said motor.*

*47. The method according to claim 46 wherein said micro-motor is cylindrical with a bore, and said guide wire is passed through said bore of said micro-motor.*

*48. The method according to claim 41 and further including withdrawing the guide wire, motor, and catheter from the lumen.*

*49. The method according to claim 48 wherein said obstruction is at or proximal to a target area of the lumen and wherein a balloon is disposed on the distal end of the catheter and further including, prior to withdrawing the guide wire, motor, and catheter from the lumen:*

*a) inflating the balloon in the target area of the lumen; and*

*b) deflating the balloon.*

*50. The method according to claim 49 wherein a stent is disposed over the balloon and the inflating of the balloon in the target area of the lumen expands the stent to dispose it in the target area.*

*51. The method according to claim 48 wherein a stent is provided at the distal end of the catheter and further comprising expanding the stent in the target area of the lumen to dispose it in the target area prior to withdrawing the guide wire, motor, and catheter from the lumen.*

*52. An apparatus, comprising: a piezoelectric motor provided with a friction area; a cylindrical guide tube defining a longitudinal bore, said motor disposed within said bore in such a manner that said friction area presses against an inner surface of said cylindrical guide tube in such a manner as to impart friction between said friction area of said motor and said inner surface in an amount sufficient to permit said cylindrical motor to change position relative to said guide tube by crawling against said inner surface of said guide tube when said motor is energized.*

*53. The apparatus of claim 52, further comprising a biasing means to bias said inner surface of said guide tube against said friction area.*

*54. The apparatus of claim 53, wherein said biasing means is a leaf spring.*

*55. The apparatus of claim 52, further comprising a device to be placed in a lumen disposed within said guide tube and contacting said motor.*

*56. A method comprising using a piezoelectric micromotor to move a device to a target area in a lumen comprising attaching said micro-motor to a catheter, frictionally engaging a guide wire that passes through said catheter with said motor and energizing said motor to bring about relative motion between the wire and catheter.*

*57. The method according to claim 56 wherein said relative motion comprises first moving the wire to a target area in a lumen with the catheter fixed and then moving the catheter to the target area while holding the guide wire fixed.*

*58. The method according to claim 57 and further including delivering a balloon on the end of said catheter to said target area and expanding said balloon at the target area.*

*59. The method according to claim 57 and further including delivering a stent on the end of said catheter to said target area and expanding said stent at the target area.*

*60. A method comprising traversing an obstruction in a lumen by causing a guide wire driven by a piezoelectric micro-motor in a oscillatory manner to advance into the obstruction including moving a catheter to which the micro-motor is attached and the guide wire to the target area using the micro-motor, holding the catheter fixed, and driving said micro-motor to cause said guide wire to advance against said obstruction in an oscillatory manner.*

*61. The method of claim 60 wherein said guide wire advances through said obstruction.*

*62. The method of claim 61 comprising alternatively advancing the catheter and the guide wire until the catheter and guide wire are clear of the obstruction.*

*63. The method according to claim 61 wherein said driving comprises energizing with an AC voltage, thereby introducing a vibration to said guide wire.*

*64. The method according to claim 63 wherein said AC voltage has a frequency in the range of 20-100 kHz.*

*65. The method according to claim 61 wherein said driving comprises energizing with an pulsed DC voltage thereby imparting a pulsating motion to said guide wire.*

* * * * *